United States Patent [19]

Rapoport

[11] 4,330,483

[45] May 18, 1982

[54] HYDROCYANATION OF OLEFINS

[75] Inventor: Morris Rapoport, Orange, Tex.

[73] Assignee: E. I. Du Pont de Nemours and Company, Wilmington, Del.

[21] Appl. No.: 237,614

[22] Filed: Feb. 24, 1981

[51] Int. Cl.³ ................ C07C 120/02; C07C 121/26
[52] U.S. Cl. .............................................. 260/465.8 R
[58] Field of Search ................................ 260/465.8 R

[56] References Cited

U.S. PATENT DOCUMENTS

| | | | |
|---|---|---|---|
| 3,496,218 | 2/1970 | Drinkard, Jr. | 260/465.3 X |
| 3,766,237 | 10/1973 | Chia et al. | 260/465.3 |
| 3,818,067 | 6/1974 | Downing et al. | 260/465.8 R |
| 3,903,120 | 9/1975 | Shook, Jr. et al. | 260/346.74 X |
| 4,082,811 | 4/1978 | Shook, Jr. | 260/465.9 X |

*Primary Examiner*—Joseph Paul Brust

[57] ABSTRACT

An improved process for the production of dinitriles, e.g., adiponitrile, by the hydrocyanation of 3 and/or 4-pentenenitriles by control of temperature and the amount of hydrogen cyanide relative to the other compounds participating in the reaction.

6 Claims, No Drawings

HYDROCYANATION OF OLEFINS

BACKGROUND OF THE INVENTION

1. Field of the Invention

The present process is directed to the production of dinitriles and more particularly, to the production of adiponitrile by the hydrocyanation of 3- and/or 4-pentenenitriles in the presence of a zero-valent nickel catalyst promoted by an organoborane.

2. Description of the Prior Art

U.S. Pat. No. 3,496,218 issued on Feb. 17, 1970 describes in general terms a process for the preparation of dinitriles especially adiponitrile by the hydrocyanation of non-conjugated, ethylenically unsaturated organic compounds, e.g., 3- and/or 4-pentenenitriles using certain nickel complexes as catalysts. The catalysts are promoted by organoborane compounds such as triphenylborane. A wide range of process conditions and relative amounts and types of reactants are disclosed.

A particularly useful form of zero-valent nickel catalyst is described in U.S. Pat. No. 3,766,237 issued on Oct. 16, 1973. The patentees disclose the use of an excess of the triarylphosphite ligand in the hydrocyanation along with the addition of certain ethers to improve the yield and increase the pounds of product which can be made per pound of catalyst consumed.

U.S. Pat. No. 4,082,811 issued on Apr. 4, 1978 discloses a hydrocyanation process coupled with a method for recovery of catalyst.

SUMMARY OF THE INVENTION

An improved process for the production of dinitriles, e.g., adiponitrile by the hydrocyanation of unsaturated nitriles, for example, 3- and/or 4-pentenenitriles in the presence of a zero-valent nickel containing catalyst promoted with an organoborane comprising maintaining the temperature of the hydrocyanation at less than about 75° C. and preferably in the range 30°–65° C., controlling the amount of hydrogen cyanide to other compounds participating in the reaction such that the overall mol ratio of hydrogen cyanide to the unsaturated nitrile is in the range of about 0.18/1 to 0.7/1, the overall mol ratio of hydrogen cyanide to zero-valent nickel catalyst in the range of about 10/1 to 116/1 and the overall mol ratio of hydrogen cyanide to promoter in the range about 30/1 to 400/1.

The preferred catalyst is represented by formula $NiL_4$ where L is $P(OAr)_3$ and Ar is mixed m,p-tolyl, e.g., tritolylphosphites (TTP). The preferred promoter is a triarylborane, e.g., triphenylborane.

In a preferred mode of operation the temperature of the hydrocyanation is maintained in the range 30°–65° C. and the overall mol ratio of hydrogen cyanide to 3- and/or 4-pentenenitriles, to zero-valent nickel catalyst and to promoter is in the range 0.25/1 to 0.55/1; 20/1 to 75/1 and 40/1 to 300/1 respectively.

DETAILED DESCRIPTION OF THE INVENTION

The present invention can be employed to produce a variety of dinitriles but adiponitrile (ADN) is of particular interest because it is an intermediate used in the production of hexamethylenediamine which in turn is used to produce polyhexamethyleneadipamide, a commercial polyamide useful in forming fibers, films and molded articles.

Although the hydrocyanation reaction can employ any non-conjugated, ethylenically unsaturated organic nitrile of from 4 to 20 carbon atoms it is of particular interest in the hydrocyanation of pentenenitriles, e.g., cis- and trans-3-pentenenitrile (3PN), 4-pentenenitrile (4PN) and mixtures thereof (3,4-PN's).

The preparation of zero-valent nickel (Ni°) catalyst which is used in the practice of the present invention is found in U.S. Pat. No. 3,903,120 issued on Sept. 2, 1975. Of particular interest is catalyst having the general formula $NiL_4$ where L is a neutral ligand such as a triarylphosphite of the formula $P(OAr)_3$ wherein Ar is an aryl group of up to 18 carbon atoms. Illustrative of the aryl groups are methoxyphenyl, tolyl, xylyl and phenyl. Meta- and para-tolyl and mixtures thereof are the preferred aryl groups. Excess ligand can be employed.

The promoters which are used with the above described catalyst are triarylboranes including those of the formula $BR_3$ wherein R is an aryl or substituted aryl group having 6 to 12 carbon atoms, e.g., phenyl, orthotolyl, para-tolyl, napthyl, methoxyphenyl, biphenyl, chlorophenyl and bromophenyl. Triphenylborane (TPB) is preferred.

The hydrocyanation can be conducted in one or more steps or stages. If a plurality of stages is employed, it is preferred that the stages be in series with the product from one stage being directed to a subsequent stage. The hydrogen cyanide can be introduced into the first stage or split between stages. It is preferred to conduct the process continuously.

The following discussion is directed to the hydrocyanation of 3PN and/or 4PN to produce ADN using Ni° catalyst containing a mixed m,p-tritolylphosphite ligand with triphenylborane (TPB) as a promoter. It is understood that the following discussion applies to other types of nitriles and catalyst.

It is well known that reaction rate can be increased by increasing reaction temperature. However, in this system, raising the temperature increases yield losses to an unacceptable level.

It has been discovered that by controlling the variables as discussed hereinbelow the yield of adiponitrile may be maximized while maintaining an acceptable production rate. More particularly, it has been found that the conversion of 3PN and/or 4PN to ADN and the temperature of the reaction have a pronounced effect on yield. For purposes of this specification the yield loss is typified by the amount of cis- and trans-2-pentenenitrile (2PN) produced.

The temperature of the reaction is a critical variable. As temperature increases yield loss, as measured by the production of 2PN, increases. The lowest temperature which can be tolerated is dependent upon the production rate desired as well as the activity of the catalyst. Usually the temperature will not be maintained below 25° C. in order to produce ADN in an acceptable yield at commercially feasible rates. At temperatures above 75° C., e.g., 100° C. it has been found that the yield loss is excessive and that no commercially practical adjustments in the reactants or other reaction variables can be made to duplicate performance at lower temperatures. Optimum results are realized when the temperature is maintained in the range of 30°–65° C.

Since substantially all of the hydrogen cyanide which is introduced in the system is reacted, i.e., at least 80% or greater it has been found that yield can be controlled by controlling the reaction temperature and addition of HCN relative to the other reactants.

The following is a discussion of the importance of the amount of HCN relative to the other compounds participating in the reaction. As the amount of HCN relative to the 3PN and/or 4PN is increased the conversion of those nitriles increases and their concentration in the reaction products decreases. This results in reduced production of 2PN and reduced yield loss. However, the amount of promoter and/or catalyst required to sustain the reaction concurrently increases which adversely affects the economics of the process. Conversely, as the amount of HCN relative to the 3PN and/or 4PN decreases the yield loss increases and the cost of recovering 3PN and/or 4PN increases. By maintaining the ratio of HCN to 3PN and/or 4PN in the range of about 0.18/1 to 0.7/1 and preferably in the range 0.25/1 to 0.55/1 the benefit of improved yield and the detriment of promoter cost and catalyst and 3,4-PN's recovery costs are balanced.

As the ratio of HCN to Ni° increases beyond 116/1 the reaction is difficult to sustain unless excessive amounts of promoter are used. Otherwise, higher temperatures are required and the yield loss increases. At ratios below 10/1 even though the reaction is vigorous and the yield loss is small, the cost of recovering the catalyst becomes excessive. The preferred balance is realized at an HCN/Ni° ratio in the range 20/1 to 75/1.

The amount of HCN relative to promoter, e.g., TPB in the reaction has been found to affect the activity of the catalyst. When the ratio of HCN/promoter exceeds 400/1 the activity of the catalyst decreases to an extent that the temperature of the reaction must be increased beyond that required to obtain an acceptable yield and unless excessive amounts of catalyst are used the yield loss to 2PN is excessive. When the ratio of HCN/promoter decreases below about 25/1 the cost of promoter is excessive. Operation at a ratio of HCN to promoter within the range of about 30/1 to 400/1 and preferably in the range 40/1 to 300/1 permits operation at an acceptable rate and temperature. Inherent in the control of the variables discussed is the maintenance of an optimum ratio of desirable pentenenitriles to undesirable nitriles, e.g., 2PN's.

The following examples are presented to illustrate but not to restrict the present invention. Parts and percentages are by weight unless otherwise noted. The following abbreviations and definitions are used in the Examples:

TTP = the reaction product of PCl$_3$ and commercially available m,p-cresol which contains minor amounts of related phenols.

$$\text{Conversion} = \frac{\text{mols of 3- and 4-PN's consumed}}{\text{mols of 3- and 4-PN's fed}} \times 100$$

$$\text{Yield (ADN)} = \frac{\text{mols of ADN produced}}{\text{mols of 3- and 4-PN's consumed}} \times 100$$

$$\text{Yield (2PN)} = \frac{\text{mols of 2-PN produced}}{\text{mols of 3- and 4-PN's consumed}} \times 100$$

The apparatus employed in all the Examples consisted of 1, 2, or 3 glass flasks as reactors of approximately 25 cc in volume which, when more than one reactor was employed, were connected in series with the overflow from the first reactor directed by gravity to the second reactor and the overflow from the second reactor directed by gravity to the third reactor. Overflow from the last reactor was retained in a product receiver which was periodically changed. Each reactor was equipped with an individually controlled electrical heating means and side arms for sampling the contents during the course of a run. The first reactor was provided with an inlet port for catalyst solution, promoter solution and pentenenitriles. Each reactor was also equipped with a port for introductions of hydrogen cyanide below the liquid contents of the flasks. A nitrogen inlet was provided to the vapor space of each reactor and the product receiver to provide a non-oxidizing atmosphere. The pentenenitriles introduced to the reactor and used to prepare the solutions described hereinbelow contained about 98% 3PN and 1% 4PN with trace amounts of other nitriles. Pentenenitriles of lesser purity can be employed with essentially similar results. Catalyst solution which was introduced into the first reactor was prepared by reacting a mixture containing 77% TTP, 20% PN's, 3% nickel powder, to which mixture had been added 100 ppm chloride catalyst as phosphorous trichloride. The mixture was heated for 16 hours at 80° C., cooled and filtered to yield a solution containing approximately 2.7% by weight zero-valent nickel (Ni°). The promoter solution was prepared by dissolving a mixture of dry TPB in the above described nitriles to yield a solution containing about 20% by weight triphenylborane. Hydrogen cyanide employed in the examples was essentially free of sulfuric acid and contained only trace amounts of sulfur dioxide. The hydrogen cyanide was cooled to about 0° C. to prevent degradation prior to introduction in the first stage (or stages). The system was started up by adding catalyst solution, pentenenitriles and promoter solution to each reactor at room temperature. Agitation was then started. After warming the reactor(s) to the indicated temperature introduction of hydrogen cyanide was commenced. When the reaction reached steady state as shown by a constant concentration of hydrogen cyanide in the reaction medium at a level indicating substantial reaction of the HCN, samples of the reactor contents and product were withdrawn and analyzed by gas chromatographic analysis to determine the amount of ADN, 3PN, 4PN and 2PN which were present therein. Failure to achieve a constant concentration of hydrogen cyanide with substantial reaction of the HCN indicates that the reaction is not operating satisfactorily. The results are reported in the Table.

TABLE

| Example No. | FEED Mol Ratio of HCN to | | | | Weight % Ni° | REACTOR TEMPERATURE (°C.) | RATE (gms ADN/cc/min × 10$^4$) | PRODUCT (wt % 3,4-PN's) | CONVERSION (%) | YIELD (% ADN) | YIELD (% 2PN) |
|---|---|---|---|---|---|---|---|---|---|---|---|
| | Ni° | TPB | TTP | 3,4-PN's | | | | | | | |
| 1 | 61.3 | 34.7 | 7.88 | 0.686$^{(8)}$ | 0.429 | 50 | 4.80 | 16.6 | 68.9 | 94.4 | 2.19 |
| 2 | 61.2 | 50.4 | 5.73 | 0.678 | 0.407 | 50 | 4.86 | 16.0 | 68.9 | 93.5 | 2.83 |
| 3 | 76.2 | 89.3 | 9.62 | 0.673 | 0.385 | 50 | 4.86 | 19.0 | 68.6 | 93.4 | 2.96 |
| 4 | 101.4 | 50.7 | 11.95 | 0.659 | 0.300 | 49.2$^{(1)}$ | 4.74 | 31.9$^{(7)}$ | 67.4 | 92.7 | 3.29 |

TABLE-continued

| Example No. | FEED | | | | Weight % Ni° | REACTOR TEMPERATURE (°C.) | RATE (gms ADN/ cc/min × 10⁴) | PRODUCT (wt % 3,4-PN's) | CONVERSION (%) | YIELD (% ADN) | YIELD (% 2PN) |
|---|---|---|---|---|---|---|---|---|---|---|---|
| | Mol Ratio of HCN to | | | | | | | | | | |
| | Ni° | TPB | TTP | 3,4-PN's | | | | | | | |
| 5 | 53.0 | 99.8 | 6.17 | 0.488 | 0.428 | 50 | 5.60 | 31.4 | 50.8 | 93.3 | 3.54 |
| 6 | 50.0 | 181.9 | 5.89 | 0.385⁽⁸⁾ | 0.362 | 46.9⁽²⁾ | 3.55 | 49.2⁽⁷⁾ | 37.9 | 92.5 | 4.00 |
| 7 | 26.2 | 98.7 | 3.04 | 0.195 | 0.375 | 50 | 4.75 | 55.8 | 20.0 | 92.2 | 5.01 |
| 8 | 26.2 | 50.2 | 3.04 | 0.196 | 0.376 | 50 | 4.88 | 54.4 | 20.8 | 91.9 | 5.13 |
| 9 | 15.7 | 145.5 | 1.89 | 0.656 | 1.065 | 60 | 2.21 | 14.7 | 58.6 | 91.8 | 3.47 |
| 10 | 38.3 | 99.6 | 2.36 | 0.480 | 0.410 | 60 | 1.35 | 23.2 | 49.5 | 92.2 | 4.36 |
| 11 | 25.0 | 390.7 | 2.90 | 0.192⁽⁸⁾ | 0.378 | 60⁽³⁾ | 3.43 | 58.4⁽⁷⁾ | 20.0 | 87.4 | 8.40 |
| 12 | 23.3 | 101.9 | 3.09 | 0.251 | 0.507 | 35 | 6.61 | 49.3 | 24.4 | 95.6 | 2.00 |
| 13 | 50.5 | 52.3⁽⁴⁾ | 6.49 | 0.484 | 0.423 | 50 | 5.58 | 31.4 | 49.2 | 92.8 | 2.71 |
| 14 | 52.0 | 121.6⁽⁵⁾ | 5.66 | 0.494 | 0.434 | 50 | 2.75 | 31.8 | 49.9 | 91.5 | 4.37 |
| 15 | 46.2 | 101.4 | 5.56⁽⁶⁾ | 0.484 | 0.491 | 50 | 2.78 | 33.0 | 49.5 | 94.2 | 2.30 |
| 16 | 47.5 | 99.7 | 6.12 | 0.484 | 0.449 | 50 | 11.23 | 30.1 | 50.2 | 92.8 | 3.82 |
| 17 | 45.0 | 96.7 | 6.11 | 0.465 | 0.457 | 60 | 10.69 | 31.7 | 48.8 | 89.7 | 6.36 |
| Comparative | 50.8 | 24.7 | 6.24 | 0.355 | 0.346 | 100 | 5.30 | 36.0 | 46.5 | 69.4 | 25.50 |

⁽¹⁾HCN fed to two reactors 71.7% to first - 28.3% second First reactor 45° C. - Second reactor 60° C. - Average 49.2
⁽²⁾HCN fed to three reactors 42.7% to first - 39.2% second - 18.1% third First reactor 45° C. - Second reacotr 47.5° C. - Third reactor 50° C. - Average 46.9° C.
⁽³⁾HCN fed to three reactors 60.3% to first - 28.5% second 11.2% thirdTemperature in each
⁽⁸⁾Tri-p-chlorophenylborane promoter
⁽⁵⁾Tri-p-tolyborane promoter feed
⁽⁶⁾Ligand prepared from PCl₃ and a 1/1 combined mol ratio mixture of phenol and m,p-cresol16 to
⁽⁸⁾Regular PN feed was combined with 1 to 0.2 parts of a stream containing about 70% 3PN and 4PN, about 10% 2PN, about 12% 2-methyl-2-butenenitrile and 8% valeronitrile Examples 1-8 and 9-11 illustrate that at a nearly constant temperature using ratios within the specified ranges, as the ratio of HCN to 3PN and/or 4PN decreases the yield to 2PN increases.

Example 12 illustrates that lowering the temperature decreases the 2PN yield and that an acceptable rate can still be obtained.

Examples 13-15 demonstrate the above-discussed effects with alternative catalyst and/or promoter systems.

Examples 16 and 17 demonstrate the effect of temperature on 2PN yield at otherwise essentially constant conditions.

The comparative shows that temperatures beyond the upper limit result in unacceptable yields.

I claim:

1. In a process for the production of dinitriles by the continuous hydrocyanation of 3- and/or 4-pentenenitriles in the presence of a zero-valent nickel containing catalyst promoted with at least one triaryl organoborane, the improvement which comprises maintaining the temperature of the hydrocyanation at less than about 75° C., the amount of hydrogen cyanide introduced into the reaction in an amount such that the mol ratio of hydrogen cyanide to the 3- and/or 4-pentenenitriles is in the range of about 0.18/1 to 0.7/1; the mol ratio of hydrogen cyanide to the zero-valent nickel catalyst is in the range of about 10/1 to 116/1 and the mol ratio of hydrogen cyanide to promoter is in the range of about 30/1 to 400/1.

2. The process of claim 1 wherein the process is conducted at a temperature in the range 30°-65° C.

3. The process of claim 1 wherein the mol ratio of hydrogen cyanide to 3- and/or 4-pentenenitriles, zero-valent nickel catalyst and promoter is in the range of 0.25/1 to 0.55/1; 20/1 to 75/1 and 40/1 to 300/1 respectively.

4. The process of claims 1, 2 or 3 wherein the zero-valent nickel catalyst has the formula NiL₄ where L is P(OAr)₃ and Ar is an aryl group of up to 18 carbon atoms and the promoter has the formula BR₃ where R is an aryl group having 6-12 carbon atoms.

5. The process of claim 4 wherein Ar is selected from the class consisting of meta-tolyl, para-tolyl and mixtures thereof and R is phenyl.

6. The process of claim 1 wherein the zero-valent nickel catalyst has the formula NiL₄ wherein L is P(OAr)₃ and Ar is selected from the class consisting of meta-tolyl, para-tolyl and mixtures thereof; the process is conducted at a temperature in the range 30°-65° C. and the mol ratio of hydrogen cyanide to 3- and/or 4-pentenenitriles, zero-valent nickel catalyst and promoter is in the range 0.25/1 to 0.55/1; 20/1 to 75/1 and 40/1 to 300/1 respectively.

* * * * *

UNITED STATES PATENT OFFICE
CERTIFICATE OF CORRECTION

PATENT NO. : 4,330,483
DATED : May 18, 1982
INVENTOR(S) : Morris Rapoport

It is certified that error appears in the above–identified patent and that said Letters Patent are hereby corrected as shown below:

Columns 5 and 6

Table:
  Example No. 12 in the column 3,4-PN's, after ".251" add footnote number -- (8) --.

In the Footnotes of the Table:
  Footnote (3), after the word "each" add -- reactor 60°C --.

First Footnote numbered "(8)" should read -- (4) --.

Footnote (6), after "1/1" delete -- combined --; and after "cresol" delete -- 16 to --.

Add Footnote "(7) Weighted average" after -- Footnote (6) --.

Columns 5 and 6, footnote (5) after "promoter" delete -- feed --.

Signed and Sealed this

Seventh Day of December 1982

[SEAL]

Attest:

GERALD J. MOSSINGHOFF

Attesting Officer        Commissioner of Patents and Trademarks